(12) United States Patent
Lee et al.

(10) Patent No.: US 12,274,540 B2
(45) Date of Patent: Apr. 15, 2025

(54) ELECTRONIC APPARATUS CAPABLE OF MEASURING BIOSIGNALS

(71) Applicant: Samsung Electronics Co., Ltd., Suwon-si (KR)

(72) Inventors: Jeehoon Lee, Suwon-si (KR); Shinhee Cho, Suwon-si (KR); Suho Lee, Suwon-si (KR); Hyunjun Jung, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 141 days.

(21) Appl. No.: 18/172,023

(22) Filed: Feb. 21, 2023

(65) Prior Publication Data

US 2023/0200673 A1     Jun. 29, 2023

Related U.S. Application Data

(63) Continuation of application No. PCT/KR2021/010051, filed on Aug. 2, 2021.

(30) Foreign Application Priority Data

Aug. 31, 2020    (KR) ........................ 10-2020-0110539

(51) Int. Cl.
    *A61B 5/0533*     (2021.01)
    *A61B 5/00*     (2006.01)
    *A61B 5/25*     (2021.01)

(52) U.S. Cl.
    CPC .............. *A61B 5/0533* (2013.01); *A61B 5/25* (2021.01); *A61B 5/68* (2013.01)

(58) Field of Classification Search
    CPC ........... A61B 5/0533; A61B 5/25; A61B 5/68; A61B 5/256; A61B 2560/0204;
(Continued)

(56) References Cited

U.S. PATENT DOCUMENTS 7,878,030 B2    2/2011   Burr
8,082,762 B2   12/2011   Burr
(Continued)

FOREIGN PATENT DOCUMENTS

JP     H06-142113 A     5/1994
JP     2014-235517 A    12/2014
(Continued)

*Primary Examiner* — Akm Zakaria
(74) *Attorney, Agent, or Firm* — Jefferson IP Law, LLP

(57) ABSTRACT

An electronic device is provided. The electronic device includes a housing including a portion of a conductive portion, a display visually exposed to an outside through a portion of the housing, a communication circuit electrically connected to the conductive portion, a sensor electrically connected to the conductive portion, a first blocking circuit connected between the conductive portion and the communication circuit and configured to block a signal in a first frequency range, a second blocking circuit connected between the conductive portion and the sensor to block a signal in a second frequency range, and a processor operatively connected to the display, the communication circuit and the sensor, wherein the conductive portion is configured to operate as an antenna of the communication circuit and a biometric electrode of the sensor.

19 Claims, 14 Drawing Sheets

(58) Field of Classification Search
CPC ........... A61B 5/291; A61B 5/30; A61B 5/681; A61B 5/0006
See application file for complete search history.

(56) References Cited

U.S. PATENT DOCUMENTS

| | | |
|---|---|---|
| 9,734,315 B2 | 8/2017 | Seol et al. |
| 9,737,221 B2 | 8/2017 | Sato |
| 9,870,716 B1 | 1/2018 | Rao et al. |
| 10,001,756 B2 | 6/2018 | Ryu et al. |
| 10,777,094 B1 | 9/2020 | Rao et al. |
| 10,892,565 B2 | 1/2021 | Wei et al. |
| 11,031,717 B2 * | 6/2021 | Cho ................... H01Q 1/243 |
| 11,064,949 B2 | 7/2021 | Bae et al. |
| 11,095,021 B2 | 8/2021 | Sung et al. |
| 11,107,368 B1 | 8/2021 | Rao et al. |
| 11,197,610 B2 | 12/2021 | Wang et al. |
| 11,394,129 B2 | 7/2022 | Wei et al. |
| 2013/0317318 A1 | 11/2013 | Tartz et al. |
| 2014/0354489 A1 | 12/2014 | Kashiwagi |
| 2016/0063232 A1 | 3/2016 | Seol et al. |
| 2017/0000374 A1 | 1/2017 | O'Neill et al. |
| 2018/0228370 A1 | 8/2018 | Wang et al. |
| 2019/0059756 A1 | 2/2019 | Rasmussen et al. |
| 2020/0015701 A1 * | 1/2020 | Wei ................... H01Q 13/10 |
| 2020/0192424 A1 | 6/2020 | Wei et al. |
| 2021/0344106 A1 | 11/2021 | Sung et al. |
| 2022/0288382 A1 * | 9/2022 | Daniels ................ A61N 1/025 |
| 2023/0199096 A1 * | 6/2023 | Yun ................... H01Q 21/08 |
| | | 455/566 |

FOREIGN PATENT DOCUMENTS

| | | |
|---|---|---|
| JP | 2016-047154 A | 4/2016 |
| JP | 2017-006230 A | 1/2017 |
| KR | 10-2015-0023466 A | 3/2015 |
| KR | 10-2016-0033935 A | 3/2016 |
| KR | 10-2017-0069766 A | 6/2017 |
| KR | 10-2017-0133668 A | 12/2017 |
| KR | 10-2018-0024336 A | 3/2018 |

* cited by examiner

ELECTRONIC APPARATUS CAPABLE OF MEASURING BIOSIGNALS

CROSS-REFERENCE TO RELATED APPLICATION(S)

This application is a continuation application, claiming priority under § 365 (c), of an International application No. PCT/KR2021/010051, filed on Aug. 2, 2021, which is based on and claims the benefit of a Korean patent application number 10-2020-0110539, filed on Aug. 31, 2020, in the Korean Intellectual Property Office, the disclosure of which is incorporated by reference herein in its entirety.

BACKGROUND

1. Field

The disclosure relates to a structure for measuring a biosignal of a user in an electronic device. More particularly, the disclosure relates to a structure of an electronic device that can commonly utilize an antenna for communication and an electrode for measuring a biosignal.

2. Description of Related Art

Recently, portable electronic devices may provide various functions in addition to a communication function with an external device. For example, as various portable electronic devices, such as smart phones and wearable devices are popular, schemes for measuring biometric information using a portable electronic device have been studied. A health care service for a user may be provided by measuring biometric information using a portable electronic device. For example, an electronic device may include a sensor for obtaining biometric information. For example, an electronic device may include at least one electrode for measuring a biosignal of a user.

The above information is presented as background information only to assist with an understanding of the disclosure. No determination has been made, and no assertion is made, as to whether any of the above might be applicable as prior art with regard to the disclosure.

SUMMARY

A plurality of electrodes may be required for an electronic device to measure a biosignal. When a separate electrode or sensor structure is included in an electronic device, the size (volume) of the electronic device may increase, or the internal design of the electronic device may be complicated and production cost may increase.

Aspects of the disclosure are to address at least the above-mentioned problems and/or disadvantages and to provide at least the advantages described below. Accordingly, an aspect of the disclosure is to provide a structure of an electronic device that can commonly utilize an antenna for communication and an electrode for measuring a biosignal.

Another aspect of the disclosure is to provide an electronic device that can commonly utilize a conductive portion included in a housing of the electronic device as an antenna and a biometric electrode without deteriorating performance of each of the biosignal measuring function and the communication function.

Additional aspects will be set forth in part in the description which follows and, in part, will be apparent from the description, or may be learned by practice of the presented embodiments.

In accordance with an aspect of the disclosure, an electronic device is provided. The electronic device includes a housing including at least a portion of a conductive portion, a display visually exposed to an outside through at least a portion of the housing, a communication circuit electrically connected to the conductive portion, a sensor electrically connected to the conductive portion, a first blocking circuit connected between the conductive portion and the communication circuit and configured to block a signal in a first frequency range, a second blocking circuit connected between the conductive portion and the sensor to block a signal in a second frequency range, and a processor operatively connected to the display, the communication circuit and the sensor, wherein the conductive portion is configured to operate as an antenna of the communication circuit and a biometric electrode of the sensor.

In accordance with another aspect of the disclosure, an electronic device is provided. The electronic device includes a housing including a first surface, a second surface facing in an opposite direction to the first surface, and a side surface including at least a portion of a conductive portion, at least one attachment member detachably attached to at least an area of the housing, a display visually exposed to an outside through at least a portion of the first surface, a sensor including at least one biometric electrode exposed to an outside through at least a portion of the second surface, a communication circuit electrically connected to the conductive portion, a sensor electrically connected to the conductive portion, a first blocking circuit connected between the conductive portion and the communication circuit to block a signal in a first frequency range, a second blocking circuit connected between the conductive portion and the sensor to block a signal in a second frequency range, and a processor operatively connected to the display, the communication circuit and the sensor, wherein the conductive portion may be configured to operate as an antenna of the communication circuit and a biometric electrode of the sensor.

According to the embodiments of the disclosure, it is possible to provide a structure capable of sharing an antenna of a communication circuit and a biometric electrode of a sensor.

According to the embodiments of the disclosure, it is possible to utilize the same conductive portions as antennas and biometric electrodes while reducing the structural space of an electronic device.

According to the embodiments of the disclosure, it is possible to efficiently provide a communication function and a biometric function of an electronic device through a conductive structure that may be commonly utilized for an antenna and a biometric electrode.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
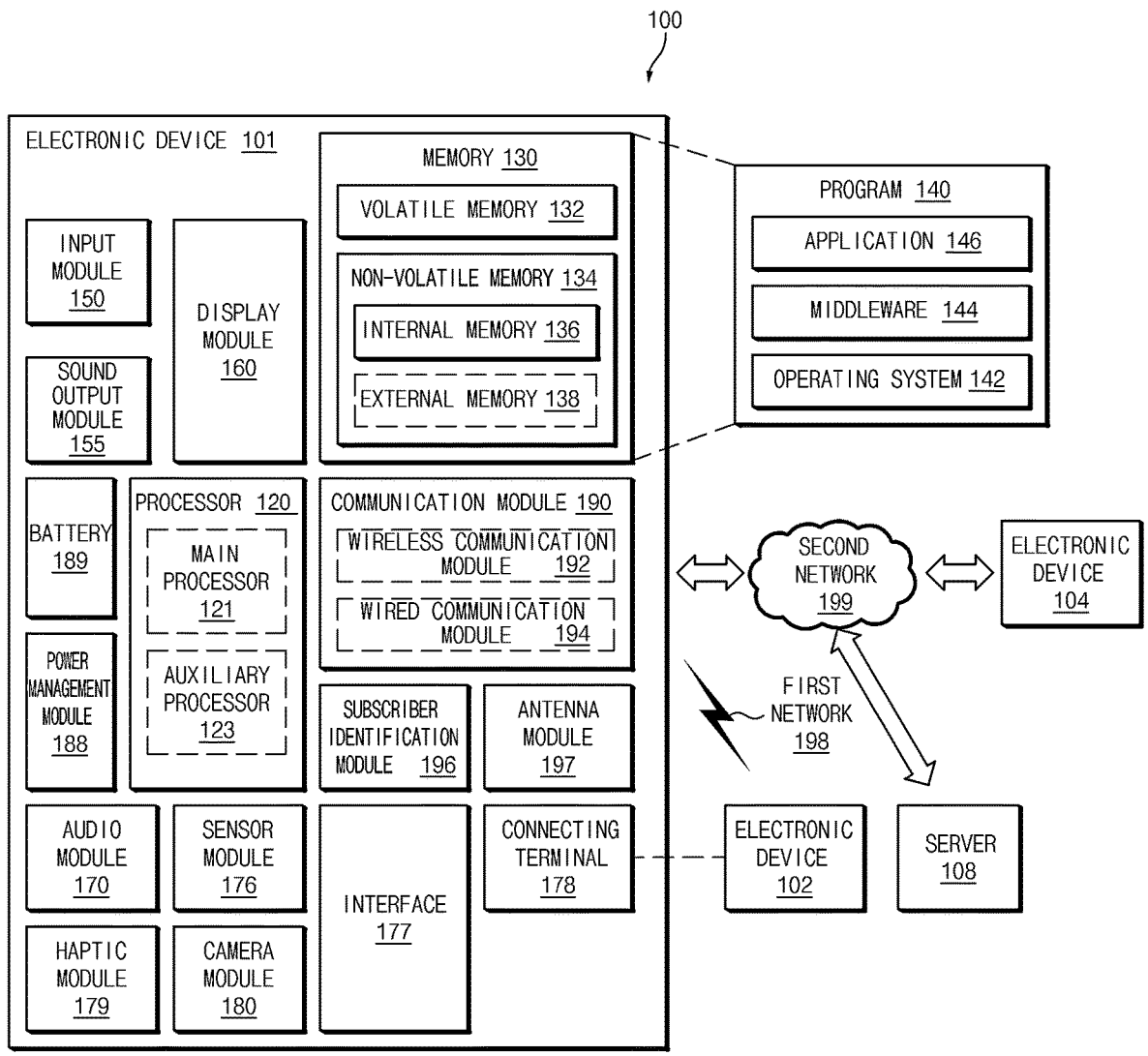
FIG. 1 is a block diagram illustrating an electronic device in a network environment according to an embodiment of the disclosure.

FIG. 1 is a block diagram illustrating an electronic device in a network environment according to an embodiment of the disclosure.

Referring to FIG. 1, the electronic device 101 in the network environment 100 may communicate with an external electronic device 102 via a first network 198 (e.g., a short-range wireless communication network), or at least one of an external electronic device 104 or a server 108 via a second network 199 (e.g., a long-range wireless communication network). According to an embodiment, the electronic device 101 may communicate with the external electronic device 104 via the server 108. According to an embodiment, the electronic device 101 may include a processor 120, a memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments, at least one of the components (e.g., the connecting terminal 178) may be omitted from the electronic device 101, or one or more other components may be added in the electronic device 101. In some embodiments, some of the components (e.g., the sensor module 176, the camera module 180, or the antenna module 197) may be implemented as a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may store a command or data received from another component (e.g., the sensor module 176 or the communication module 190) in a volatile memory 132, process the command or the data stored in the volatile memory 132, and store resulting data in a non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., a sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment, the display module 160 may include a touch sensor adapted to detect a touch, or a pressure sensor adapted to measure the intensity of force incurred by the touch.

The audio module 170 may convert a sound into an electrical signal and vice versa. According to an embodiment, the audio module 170 may obtain the sound via the input module 150, or output the sound via the sound output module 155 or a headphone of an external electronic device (e.g., the external electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the external electronic device 102) directly (e.g., wiredly) or wirelessly. According to an embodiment, the interface 177 may include, for example, a high-definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the external electronic device 102). According to an embodiment, the connecting terminal 178 may include, for example, a HDMI connector, a USB connector, an SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the external electronic device 102, the external electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a fifth generation (5G) network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a fourth generation (4G) network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the millimeter wave (mm Wave) band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large-scale antenna. The wireless communication module 192 may support various requirements specified in the electronic device 101, an external electronic device (e.g., the external electronic device 104), or a network system (e.g., the second network 199). According to an embodiment, the wireless communication module 192 may support a peak data rate (e.g., 20 gigabits per second (Gbps) or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., a printed circuit board (PCB)). According to an embodiment, the antenna module 197 may include a plurality of antennas (e.g., array antennas). In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

According to various embodiments, the antenna module 197 may form a mm Wave antenna module. According to an embodiment, the mm Wave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the external electronic devices 102 or 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., a smart home, a smart city, a smart car, or healthcare) based on 5G communication technology or IoT-related technology.

Figure 2A:
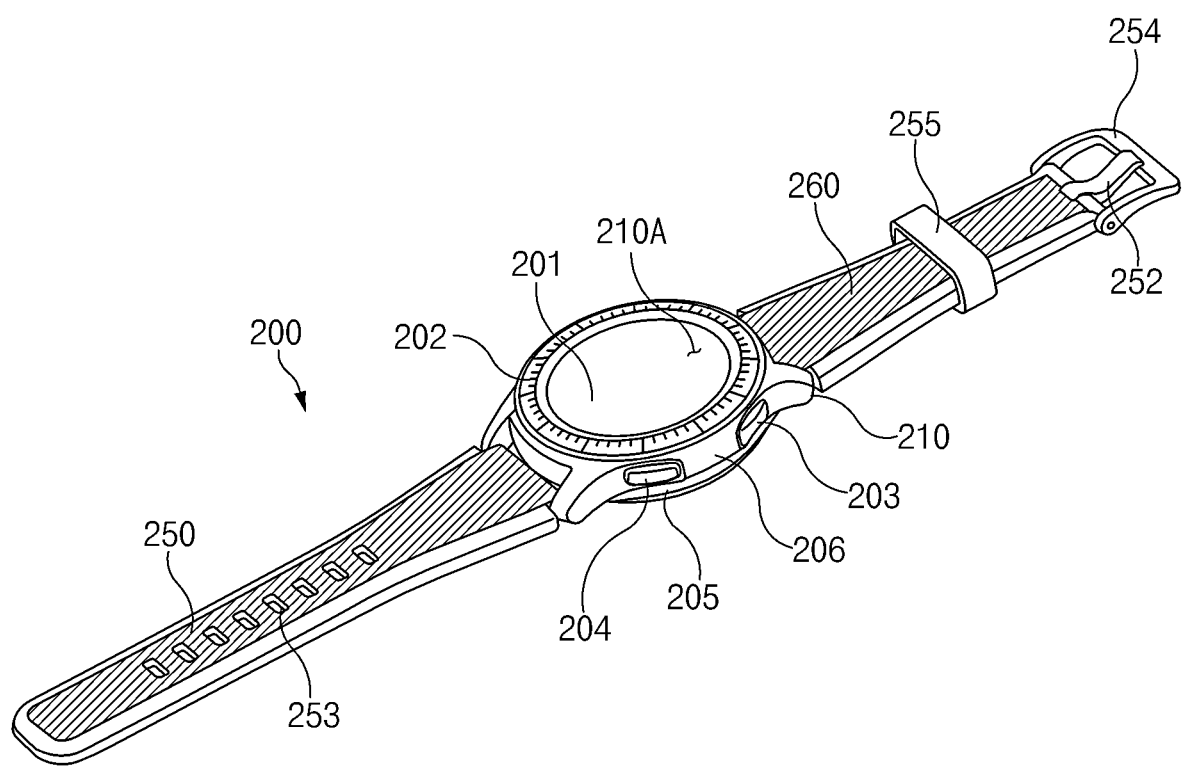
FIGS. 2A and 2B are perspective views of an electronic device according to various embodiments of the disclosure.
Figure 2B:
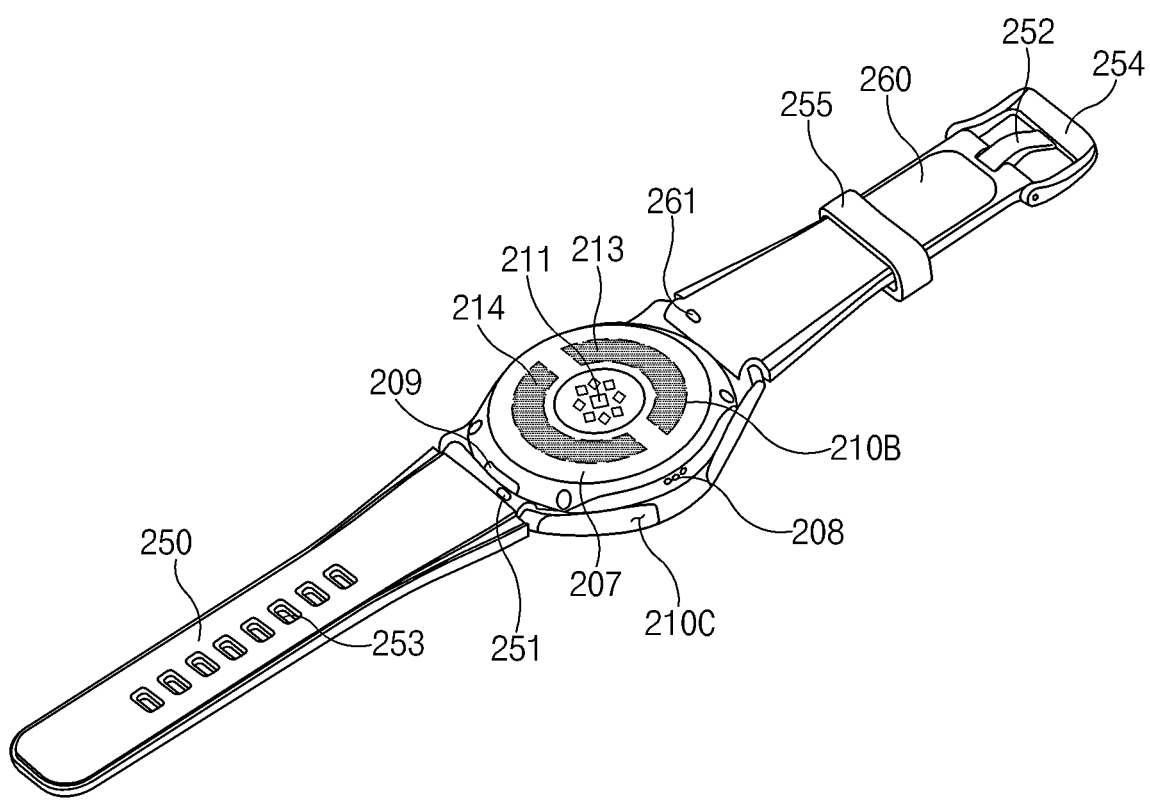

FIGS. 2A and 2B are perspective views of an electronic device according to various embodiments of the disclosure.

Referring to FIGS. 2A and 2B, an electronic device 200 (e.g., the electronic device 101 of FIG. 1) according to an embodiment may include a housing 210 including a first surface (or front surface) 210A, a second surface (or rear surface) 210B, and a side surface 210C surrounding a space between the first surface 210A and the second surface 210B, and attachment members 250 and 260 connected to at least a portion of the housing 210 and detachably attaching the electronic device 200 to a body part (e.g., wrist, ankle, or the like) of a user. In another embodiment (not shown), the housing may refer to a structure that forms a portion of the first surface 210A, the second surface 210B and the side surface 210C of FIGS. 2A and 2B. According to an embodiment, the first surface 210A may be formed by a front plate 201 (e.g., a glass plate or a polymer plate including various coating layers) that is substantially transparent at least in part. The second surface 210B may be formed by a substantially opaque rear plate 207. The rear plate 207 may be formed of, for example, coated or tinted glass, ceramic, polymer, metal (e.g., aluminum, stainless steel (STS), or magnesium), or a combination of at least two of the above-mentioned materials. The side surface 210C may be coupled to the front plate 201 and the rear plate 207 and may be formed by a side bezel structure (or "side member") 206 including metal and/or polymer. In some embodiments, the rear plate 207 and the side bezel structure 206 may be integrally formed and include the same material (e.g., a metal material, such as aluminum). The attachment members 250 and 260 may be formed of various materials and shapes. Integral and plurality of unit links may be formed to be moveable relatively to each other by woven material, leather, rubber, urethane, metal, ceramic, or a combination of at least two of the above-mentioned materials.

According to an embodiment, the electronic device 200 may include at least one of a display 220 (see FIG. 3), audio modules 205 and 208, a sensor module 211, key input devices 202, 203 and 204, and a connector hole 209. In an embodiment, the electronic device 200 may omit at least one of components (e.g., the key input devices 202, 203 and 204, the connector hole 209, or the sensor module 211) or additionally include other components.

For example, the display 220 may be exposed through a significant portion of the front plate 201. The shape of the display 220 may be a shape corresponding to the shape of the front plate 201, and may have various shapes, such as a circular shape, an elliptical shape, a polygonal shape, or the like. The display 220 may be coupled to or arranged adjacent to a touch sensing circuit, a pressure sensor capable of measuring the intensity (pressure) of a touch, and/or a fingerprint sensor.

The audio modules 205 and 208 may include the microphone hole 205 and the speaker hole 208. A microphone for acquiring external sound may be arranged inside the microphone hole 205, and in an embodiment, a plurality of microphones may be arranged to detect the direction of sound. The speaker hole 208 may be used as an external speaker and a receiver for a call. In an embodiment, the speaker hole 208 and the microphone hole 205 may be implemented as one hole, or a speaker (e.g., a piezo speaker) may be included without the speaker hole 208.

The sensor module 211 may generate an electrical signal or data value corresponding to an internal operating state of the electronic device 200 or an external environmental state. For example, the sensor module 211 may include the biometric sensor module 211 (e.g., a heart rate monitor (HRM) sensor) arranged on the second surface 210B of the housing 210. The electronic device 200 may further include a sensor module not shown, for example, at least one of a gesture sensor, a gyro sensor, an air pressure sensor, a magnetic sensor, an acceleration sensor, a grip sensor, a color sensor, an infrared (IR) sensor, a biometric sensor, a temperature sensor, a humidity sensor, or an illuminance sensor.

The sensor module 211 may include electrode regions 213 and 214 forming a portion of the surface of the electronic device 200 and a biosignal detection circuit (not shown) electrically connected to the electrode regions 213 and 214. For example, the electrode regions 213 and 214 may include the first electrode region 213 and the second electrode region 214 arranged on the second surface 210B of the housing 210. The sensor module 211 may be configured such that the electrode regions 213 and 214 obtain an electrical signal from a portion of the user's body and the biosignal detection circuit detects the user's biometric information based on the electrical signal.

The key input devices 202, 203 and 204 may include a wheel key 202 arranged on the first surface 210A of the housing 210 and rotatable in at least one direction, and/or side key buttons 203 and 204 arranged on the side surface 210C of the housing 210. The wheel key may have a shape corresponding to the shape of the front plate 202. In another embodiment, the electronic device 200 may not include some or all of the above-mentioned key input devices 202, 203 and 204, and the key input devices 202, 203 and 204 that are not included may be implemented on the display 220 in other forms, such as soft keys. The connector hole 209 may accommodate a connector (e.g., a USB connector) for transmitting and receiving power and/or data to and from an external electronic device and another connector hole (not shown) that accommodates a connector for transmitting and receiving an audio signal to and from an external electronic device. For example, the electronic device 200 may further include a connector cover (not shown) that covers at least a portion of the connector hole 209 and blocks external foreign substances from being input into the connector hole.

The attachment members 250 and 260 may be detachably attached to at least a portion of the housing 210 by using locking members 251 and 261. The attachment members 250 and 260 may include one or more of a fixing member 252, a fixing member fastening hole 253, a band guide member 254, and a band fixing ring 255.

The fixing member 252 may be configured to fix the housing 210 and the attachment members 250 and 260 to a portion (e.g., wrist, ankle, or the like) of the user's body. The fixing member fastening hole 253 may fix the housing 210 and the attachment members 250 and 260 to a portion of the user's body corresponding to the fixing member 252. The band guide member 254 may be configured to limit the movement range of the fixing member 252 when the fixing member 252 is fastened with the fixing member fastening hole 253, such that the attachment members 250 and 260 are tightly attached to a portion of the user's body. The band fixing ring 255 may limit the movement range of the attachment members 250 and 260 in a state in which the fixing member 252 and the fixing member fastening hole 253 are fastened.

Figure 3:
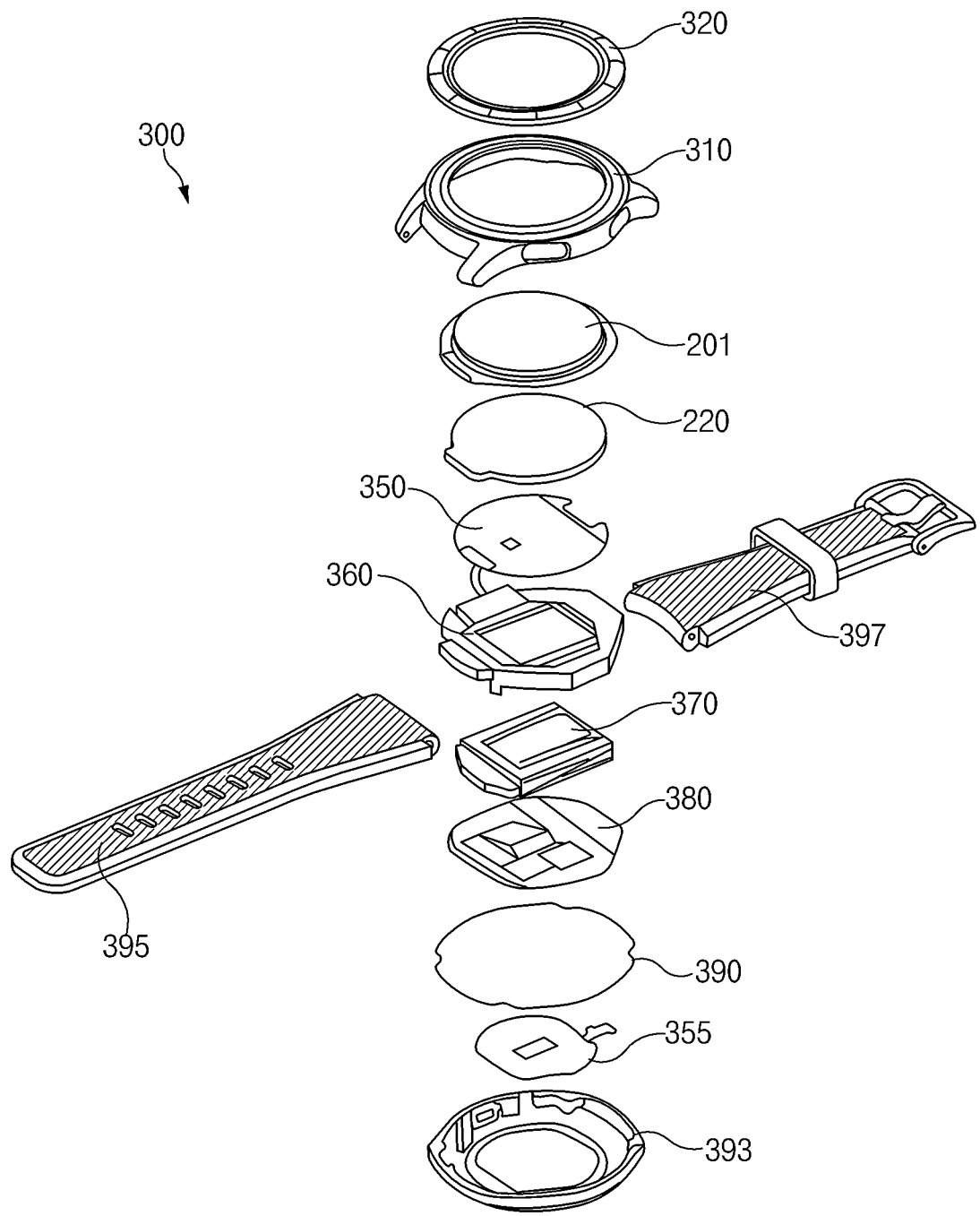
FIG. 3 is an exploded perspective view of an electronic device according to an embodiment of the disclosure.

FIG. 3 is an exploded perspective view of an electronic device according to an embodiment of the disclosure.

Referring to FIG. 3, an electronic device 300 (e.g., the electronic device 101 of FIG. 1 or the electronic device 200 of FIGS. 2A and 2B) may include a side bezel structure 310, a wheel key 320, the front plate 201, the display 220, a first antenna 350, a second antenna 355, a support member 360 (e.g., bracket), a battery 370, a printed circuit board 380, a sealing member 390, a rear plate 393, and attachment members 395 and 397. At least one of the components of the electronic device 300 may be the same as or similar to at least one of the components of the electronic device 200 of FIG. 1 or 2, and overlapping descriptions will be omitted below. The support member 360 may be arranged inside the electronic device 300 and connected to the side bezel structure 310 or integrally formed with the side bezel structure 310. For example, the support member 360 may be formed of a metal material and/or a non-metal material (e.g., polymer). The support member 360 may have one surface coupled to the display 220 and an opposite surface coupled to the printed circuit board 380. A processor, a memory, and/or an interface may be mounted on the printed circuit board 380. For example, the processor may include one or more of a central processing unit, an application processor, a graphic processing unit (GPU), an application processor, a sensor processor, or a communication processor.

For example, the memory may include a volatile memory or non-volatile memory. The interface may include, for example, a high-definition multimedia interface (HDMI), a universal serial bus (USB) interface, an SD card interface, and/or an audio interface. For example, the interface may electrically or physically connect the electronic device 300 to an external electronic device, and may include a USB connector, an SD card/multimedia card (MMC) connector, or an audio connector.

The battery 370 is a device for supplying power to at least one component of the electronic device 300, and includes, for example, a non-rechargeable primary battery, a rechargeable secondary battery, or a fuel cell. For example, at least a portion of the battery 370 may be arranged on substantially the same plane as the printed circuit board 380. The battery 370 may be integrally arranged inside the electronic device 200 or may be arranged detachably from the electronic device 200.

The first antenna 350 may be arranged between the display 220 and the support member 360. The first antenna 350 may include, for example, a near field communication (NFC) antenna, a wireless charging antenna, and/or a magnetic secure transmission (MST) antenna. For example, the first antenna 350 may perform short-range communication with an external device, wirelessly transmit/receive power required for charging, and transmit a short-range communication signal or a magnetic-based signal including payment data. In another embodiment, an antenna structure may be formed by a portion of the side bezel structure 310 and/or the support member 360 or a combination thereof.

The second antenna 355 may be arranged between the printed circuit board 380 and the rear plate 393. For example, the second antenna 355 may include a near field communication (NFC) antenna, a wireless charging antenna, and/or a magnetic secure transmission (MST) antenna. For example, the second antenna 355 may perform short-range communication with an external device, wirelessly transmit/receive power required for charging, and transmit a short-range communication signal or a magnetic-based signal including payment data. In another embodiment, an antenna structure may be formed by a portion of the side bezel structure 310 and/or the rear plate 393 or a combination thereof.

The sealing member 390 may be positioned between the side bezel structure 310 and the rear plate 393. The sealing member 390 may be configured to block moisture and foreign substances from entering into the space surrounded by the side bezel structure 310 and the rear plate 393 from an outside.

Figure 4:
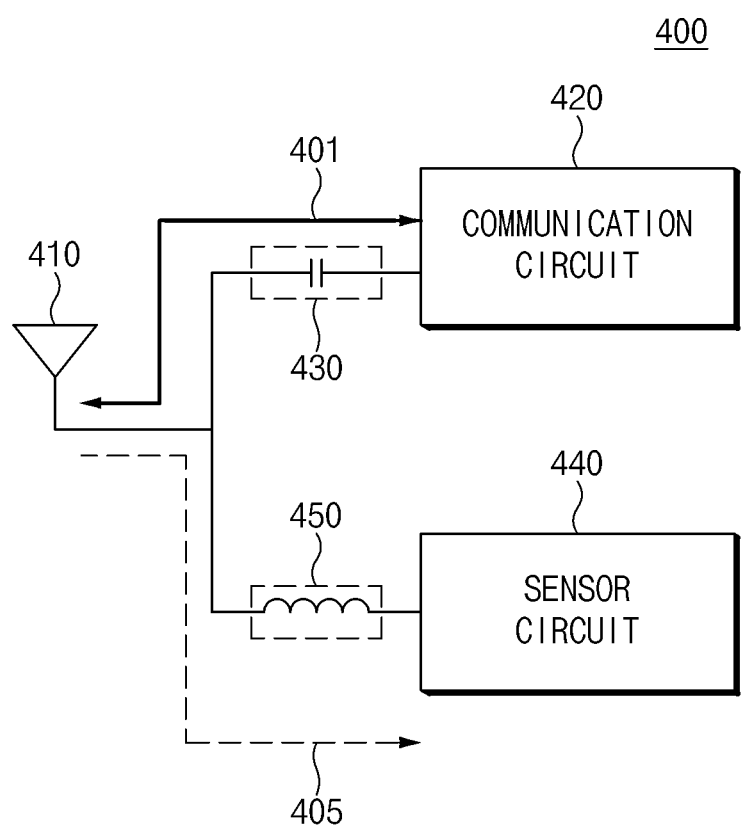
FIG. 4 is a diagram illustrating a connection structure of internal components of an electronic device according to an embodiment of the disclosure.

FIG. 4 illustrates a connection structure of internal components of an electronic device according to an embodiment of the disclosure.

Referring to FIG. 4, according to an embodiment, an electronic device 400 (e.g., the electronic device 101 of FIG. 1, the electronic device 200 of FIGS. 2A to 2B, and/or the electronic device 300 of FIG. 3) may include a housing (not shown) including a conductive portion 410 (e.g., the housing 210 of FIGS. 2A and 2B), a communication circuit 420 (e.g., the communication module 190 of FIG. 1), a sensor circuit 440 (e.g., the sensor module 176 of FIG. 1 or the sensor 211 of FIGS. 2A and 2B), a first blocking circuit 430, and/or a second blocking circuit 450.

According to an embodiment, the conductive portion 410 may be configured to form at least a portion of a side surface (e.g., the side surface 210C of FIGS. 2A and 2B) of the housing of the electronic device 400. For example, the conductive portion 410 may constitute at least a portion of a bezel (e.g., the bezel structure 206 of FIGS. 2A and 2B or the side bezel structure 310 of FIG. 3) of the electronic device 400. According to an embodiment, the conductive portion 410 may include a first conductive portion and a second conductive portion spaced apart from each other. For example, the first conductive portion and the second conductive portion may be electrically insulated from each other. For example, the first conductive portion and the second conductive portion may be segmented by a non-conductive portion. For example, the non-conductive portion may be arranged between the first conductive portion and the second conductive portion. For example, the non-conductive portion may be formed of a non-conductive material (e.g., polycarbonate (PC)). According to an embodiment, each of the conductive portion 410 and the non-conductive portion of the housing may be formed of a different material (conductive material or non-conductive material), or a portion exposed to an outside may be coated with a conductive material or a non-conductive material.

According to an embodiment, the sensor circuit 440 may be electrically connected to the conductive portion 410 and/or at least one electrode (e.g., the first electrode region 213 or the second electrode region 214 of FIG. 2B) included in the electronic device 400. According to an embodiment, the sensor circuit 440 may include a sensor for measuring a biosignal together with the conductive portion 410 and/or at least one electrode included in the electronic device 400. According to an embodiment, the sensor circuit 440 may include a configuration of a series of elements for operating the sensor. According to an embodiment, the conductive portion 410 may operate as at least one electrode for measuring a biosignal. For example, the sensor circuit 440 may use the conductive portion 410 and an electrode (e.g., the first electrode region 213 or the second electrode region 214 of FIG. 2B) separated from the conductive portion 410 to measure a biosignal of a user. For example, when the user's body contacts electrodes for measuring a plurality of biosignals, the plurality of electrodes and the user's body may constitute one closed circuit. For example, the sensor circuit 440 may measure the biosignal of a user based on the first electrode region and the second electrode region. For example, the biosignal may include an electrocardiogram (ECG), a galvanic skin response (GSR), an electroencephalogram (EEG), or a bioelectrical impedance analysis (BIA) signal. According to various embodiments, the biosignal may include various biosignals other than ECG, GSR, EEG, and BIA. For example, the electronic device 400 (e.g., the sensor circuit 440) may further include an electrode (e.g., the first electrode region 213 or the second electrode region 214 of FIG. 2B), or a manipulation unit (not shown, e.g., the key input devices 202, 203 and 204 of FIGS. 2A and 2B) arranged on a portion of the housing and including a conductor. According to an embodiment, the sensor circuit 440 may measure the biosignal of a user by using the conductive portion 410 and at least one electrode provided separately from the conductive portion 410.

According to an embodiment, the communication circuit 420 may be electrically connected to the conductive portion 410. According to an embodiment, the conductive portion 410 may operate as a radiator of an antenna (e.g., the antenna module 197 of FIG. 1, or the first antenna 350 or the second antenna 355 of FIG. 3) of the communication circuit 420. According to an embodiment, the communication circuit 420 may transmit/receive signals to/from an external device through the conductive portion 410.

According to an embodiment, the first blocking circuit 430 may be connected between the conductive portion 410 and the communication circuit 420. According to an embodiment, the first blocking circuit 430 may include at least one passive element (e.g., a capacitor). According to an embodiment, the first blocking circuit 430 may block a signal in the first frequency range. For example, the first blocking circuit 430 may block a signal (e.g., a biosignal 405 measured by a sensor) in the first frequency range that is not used for wireless communication with an external device. For example, the first blocking circuit 430 may block a low-frequency signal of a specified value or less. According to an embodiment, the first blocking circuit 430 may block signals in a plurality of specified first frequency ranges.

According to an embodiment, the second blocking circuit 450 may be connected between the conductive portion 410 and the sensor circuit 440. According to an embodiment, the second blocking circuit 450 may include at least one passive element (e.g., an inductor). According to an embodiment, the second blocking circuit 450 may block a signal in the second frequency range. According to an embodiment, the second frequency range may be higher than the first frequency range. For example, the second blocking circuit 450 may block a signal (e.g., a communication signal 401 used in the communication circuit, a cellular communication signal, a short-distance wireless communication signal, or a GNSS communication signal) in the second frequency range used for wireless communication with an external device. For example, the second blocking circuit 450 may block a high frequency signal exceeding a specified value. According to an embodiment, the second blocking circuit 450 may block signals in a plurality of specified second frequency ranges.

According to an embodiment, when the conductive portion 410 includes a plurality of sub conductive portions (e.g., the first conductive portion and the second conductive portion), the first blocking circuit 430 may be connected between each of the plurality of sub conductive portions 410 and the communication circuit 420 and the second blocking circuit 450 may be connected between each of the plurality of sub conductive portions 410 and the sensor 440.

For example, the frequency band of an antenna for long term evolution (LTE), Bluetooth, and/or global navigation satellite system (GNSS) communication may be a hundred of megahertz (MHz) band or several gigahertz (GHz) band, and the measurement frequency band of a biosignal (e.g., electrocardiogram) may be different in frequency band being several tens of hertz (Hz). According to an embodiment, the first blocking circuit 430 may block a signal in a frequency band for measuring a biosignal, and the second blocking circuit 450 may block a signal in a frequency band for communication with an external device. According to an embodiment, because the frequency band blocked by the first blocking circuit 430 is different from the frequency band blocked by the second blocking circuit 450, when the communication circuit 420 and the sensor circuit 440 are connected to one conductive portion 410, compared to the case where the communication circuit 420 and the sensor circuit 440 are connected to different conductive portions (not shown), the communication performance of the communication circuit 420 and the biosignal measurement performance of the sensor circuit 440 may be the same as or similar. For example, by configuring the first blocking circuit 430 and the second blocking circuit 450 with passive elements that are small in size (volume) and inexpensive, the conductive portion 410 included in the housing of the electronic device 400 may be commonly utilized as an antenna of the communication circuit 420 and a measurement electrode of the sensor circuit 440 without additional elements (e.g., switches), so that it is possible to efficiently configure the internal space of the electronic device 400. As a comparative example, when a switch (e.g., a radio frequency (RF) switch) is connected to the location of the first blocking circuit 430, the performance of the sensor 440 may be deteriorated due to the low impedance characteristics of the RF switch. When a switch (e.g., an analog switch) is connected to the location of the first blocking circuit 430 or the second blocking circuit 450, because the communication circuit 420 is required to be opened when the sensor circuit 440 is used, the communication circuit 420 and the sensor circuit 440 may not be used simultaneously. According to an embodiment of the disclosure, the first blocking circuit 430 and the second blocking circuit 450 are configured with passive elements without using an element, such as a switch, and the same conductive portion 410 is used in common. The internal space of the electronic device 400 can be efficiently utilized and the communication circuit 420 and the sensor circuit 440 can operate simultaneously. According to an embodiment, when the electronic device 400 detects that the user's body is in contact with the conductive portion 710 through the sensor circuit 440, the electronic device 400 may reduce radiated power of the communication circuit 420. For example, the electronic device 400 may reduce the amount of electromagnetic waves applied to the user by reducing the radiated power of the communication circuit 420 while measuring the user's biosignal through the sensor circuit 440.

Figure 5A:
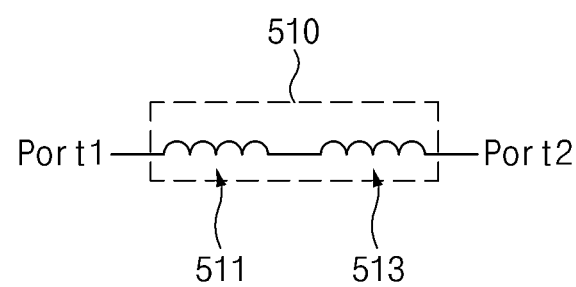
FIGS. 5A and 5B are diagrams illustrating an operation and an operation result of an electronic device according to various embodiments of the disclosure.
Figure 5B:
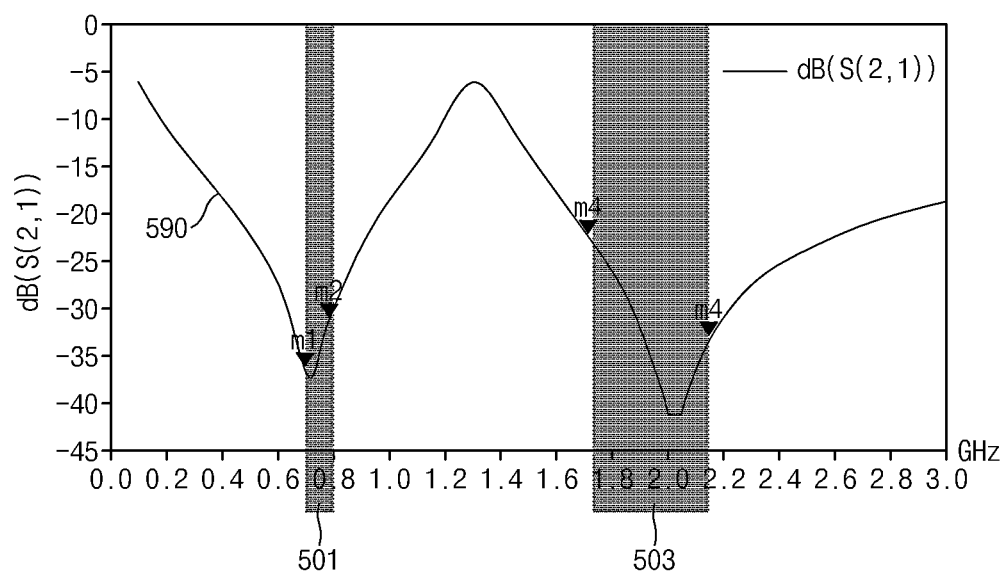

FIGS. 5A and 5B are diagrams illustrating an operation and an operation result of an electronic device according to various embodiments of the disclosure.

FIG. 5A illustrates one example of a blocking circuit 510 (e.g., the first blocking circuit 430 or the second blocking circuit 450 of FIG. 4) of an electronic device according to an embodiment (e.g., the electronic device 101 of FIG. 1, the electronic device 200 of FIGS. 2A to 2B, the electronic device 300 of FIG. 3, or the electronic device 400 of FIG. 4). According to an embodiment, the blocking circuit 510 may be connected between a conductive portion (e.g., the conductive portion 410 of FIG. 4) of a housing (e.g., the housing 210 of FIGS. 2A and 2B) and a sensor (e.g., the sensor module 176 of FIG. 1, the sensor 211 of FIGS. 2A and 2B, or the sensor 440 of FIG. 4) of an electronic device. For example, the conductive portion of the housing may be electrically connected to a first port Port 1 of the blocking circuit 510, and the sensor may be connected to a second port Port 2 of the blocking circuit 510. According to an embodiment, the blocking circuit 510 may include one or more passive elements (e.g., a first inductor 511 and a second inductor 513). According to an embodiment, inductance values of the first inductor 511 and the second inductor 513 may be set to correspond to at least one band to be blocked through the blocking circuit 510. For example, the blocking frequency of the blocking circuit 510 may be determined according to inductance values of the first inductor 511 and the second inductor 513. For example, the inductance values of the first inductor 511 and the second inductor 513 may be determined to correspond to a band through which a communication circuit (e.g., the communication module 190 in FIG. 1 or the communication circuit 420 in FIG. 4) communicates with an external device. For example, the inductance values of the first inductor 511 and the second inductor 513 may correspond to a frequency range of an LTE communication band, a Bluetooth communication band, and/or a GNSS communication band.

For example, FIG. 5B is a graph illustrating the magnitude of a signal transmitted to a sensor connected to the blocking circuit 510 when the value of the first inductor 511 is 200 nH and the value of the second inductor 513 is 47 nH. For example, bands 501 and 503 may correspond to the LTE band. For example, the band 501 may include band B12 (698 MHz to 746 MHZ) and/or band B13 (746 MHz to 787 MHz), and the band 503 may include band B2 (1850 MHz to 1990 MHZ) and/or band B4 (1710 MHz to 2155 MHz). According to various embodiments, the communication band is not limited to those described in FIGS. 5A and 5B, and may be designated or set as a desired band by adjusting the configuration and element values of the blocking circuit.

TABLE 1

| Frequency | Band 501 | | Band 503 | |
|---|---|---|---|---|
| (MHz) | 699(m1) | 787(m2) | 1710(m3) | 2155(m4) |
| S(2, 1) (dB) | −36.5 | −31.1 | −22.1 | −32.97 |

According to an embodiment, the blocking circuit 510 may block transmission of a signal of a frequency used for communication through a communication circuit to a sensor when the communication circuit and the sensor are connected to the conductive portion of the housing. For example, referring to S(2, 1), graph 590 and Table 1, in the bands 501 and 503, the S (2, 1) value has a relatively lower value than the bands other than the bands 501 and 503. For example, referring to the graph 590 and Table 1, S(2, 1) at frequency m1, which is the boundary of the band 501, is −36.5 dB, S(2, 1) at frequency m2 is −31.1 dB, S(2, 1) at frequency m3, which is the boundary of the band 503, is −22.1 dB, and S(2, 1) at frequency m4 is −32.97 dB. Compared to the fact that S(2, 1) in bands other than the bands 501 and 503 is about −20 dB or more, S(2, 1) in the bands 501 and 503 has a relatively lower value than that in the bands other than the bands 501 and 503, which may indicate that the signal of the band used for wireless communication is blocked by the blocking circuit 510 without being transmitted to the sensor. For example, the blocking circuit 510 may prevent signals of the bands 501 and 503 used for communication with external devices from being transmitted to the sensor, so that it is possible to prevent the performance of the sensor from being deteriorated due to the communication signal while the communication circuit and the sensor are connected to the same conductive portion, and the communication circuit transmits/receives communication signals through the conductive portion. When the sensor and the communication circuit are connected to the conductive portion using the blocking circuit 510, the electronic device according to an embodiment may allow the conductive portion to operate simultaneously as the antenna of the communication circuit and the biometric electrode of the sensor while preventing communication performance and sensor performance of the electronic device from deteriorating. FIGS. 5A and 5B illustrate an example in which a sensor is connected to the second port of the blocking circuit 510, but the embodiment is not limited thereto. According to an embodiment, the blocking circuit 510 may be connected between a conductive portion (e.g., the conductive portion 410 of FIG. 4) of the housing of the electronic device and a communication circuit (e.g., the communication circuit 420 of FIG. 4). For example, the conductive portion of the housing may be electrically connected to the first port Port 1 of the blocking circuit 510, and the communication circuit may be connected to the second port Port 2 of the blocking circuit 510. According to an embodiment, the blocking circuit 510 may include one or more passive elements (e.g., a first capacitor and a second capacitor).

Figure 6:
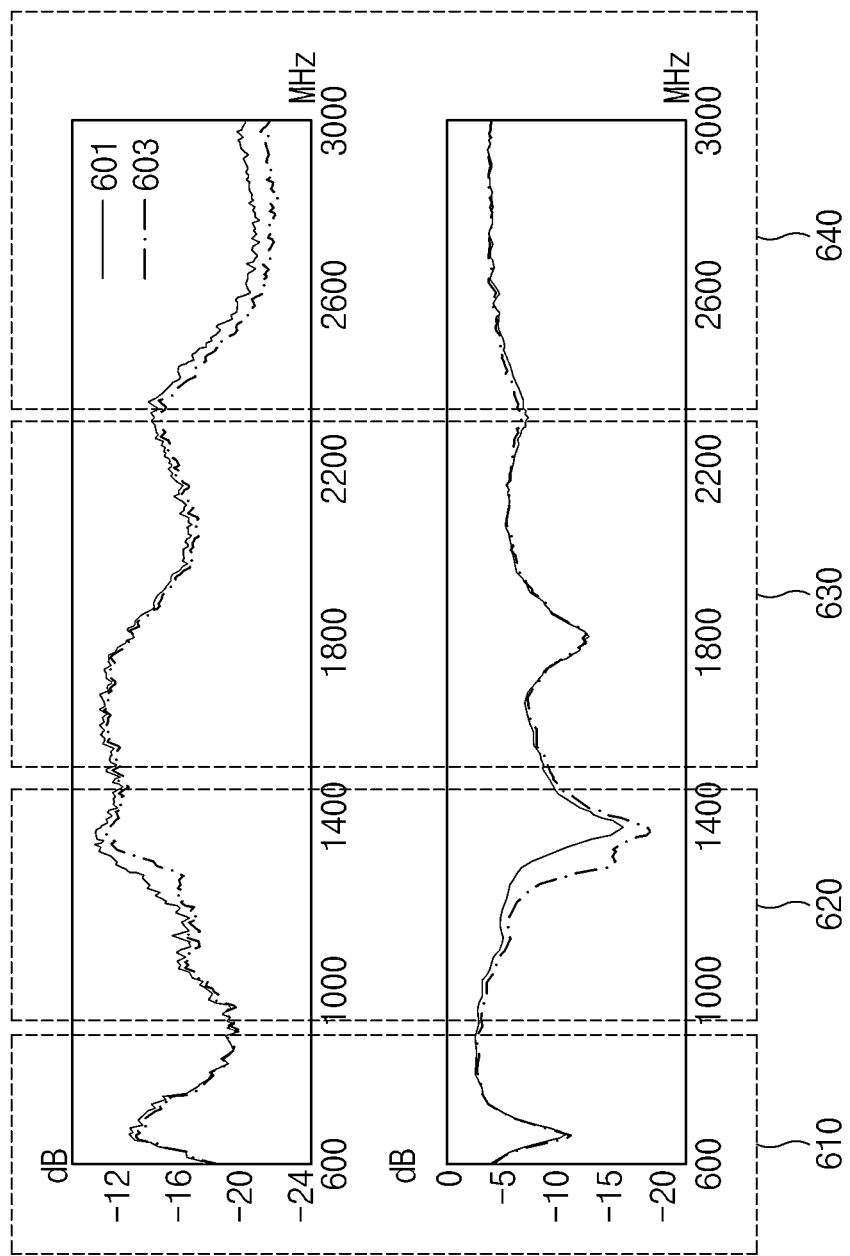
FIG. 6 is a diagram illustrating an operation and an operation result of an electronic device according to an embodiment of the disclosure.

FIG. 6 is a diagram illustrating an operation and an operation result of an electronic device (e.g., the electronic device 101 of FIG. 1, the electronic device 200 of FIGS. 2A to 2B, the electronic device 300 of FIG. 3, or the electronic device 400 of FIG. 4) according to an embodiment of the disclosure.

For example, the upper graph of FIG. 6 represents the efficiency of an antenna (e.g., the conductive portion of the housing), and the lower graph represents the reflection coefficient. For example, unlike an embodiment of the disclosure, graph 601 represents a value when a conductive portion (e.g., an antenna) and a communication circuit are connected without a blocking circuit. Graph 603 according to an embodiment of the disclosure represents a value when a blocking circuit (e.g., the blocking circuit of FIG. 5A) is connected between the conductive portion and the sensor. For example, a frequency band (e.g., long-term evolution (LTE) band) used for communication with an external device in a communication circuit may be a band 610 (e.g., 600 to 900 MHz) and a band 630 (e.g., 1.5 to 2.3 GHZ). For example, bands 620 and 640 may not be used for communication with an external device.

According to an embodiment, the band blocked by the blocking circuit (e.g., the first blocking circuit 430 or the second blocking circuit 450 of FIG. 4 or the blocking circuit 510 of FIG. 5A) may be changed according to the values of passive elements constituting the blocking circuit. For example, the frequency ranges of the bands 610 and 630 may be changed according to passive elements constituting the blocking circuit.

Comparing the graphs 601 and 603, in the bands 610 and 630 for communication with an external device, the values in the case where there is no blocking circuit and the case where the blocking circuit is connected are substantially the same. In bands 620 and 640, which are not used for communication with external devices, values may be relatively different between a case without a blocking circuit and a case where a blocking circuit is connected. For example, in the bands 610 and 630 used for communication, it may be confirmed that the communication performance is not deteriorated even when a blocking circuit is connected. According to an embodiment, when the blocking circuit is connected between the conductive portion of the housing and the sensor, the electronic device may allow the communication performance of the communication circuit to be maintained by properly setting the values of the passive elements constituting the blocking circuit even when the sensor and the communication circuit are connected together to the conductive portion. When the sensor and the communication circuit are connected to the conductive portion using a blocking circuit, the electronic device according to an embodiment may allow the conductive portion to simultaneously operate as the antenna of the communication circuit and the biometric electrode of the sensor while preventing the communication performance and sensor performance of the electronic device from deteriorating.

Figure 7:
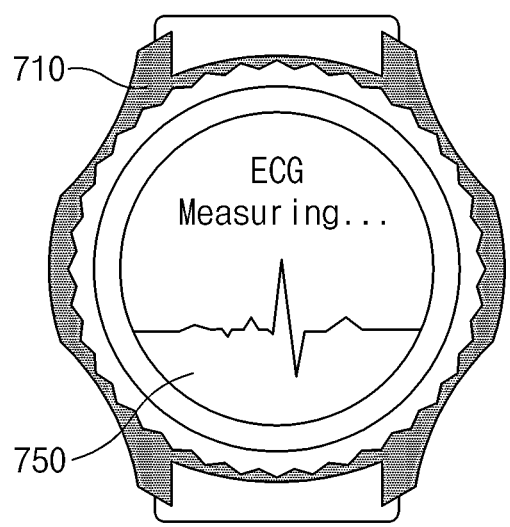
FIG. 7 illustrates an electronic device according to an embodiment of the disclosure.

FIG. 7 illustrates an electronic device according to an embodiment of the disclosure.

Referring to FIG. 7, according to an embodiment, an electronic device 700 (e.g., the electronic device 101 of FIG. 1, the electronic device 200 of FIGS. 2A and 2B, the electronic device 300 of FIG. 3, or the electronic device 400 of FIG. 4) may include a housing (e.g., the housing 210 of FIGS. 2A and 2B), a sensor (not shown, e.g., the sensor module 176 in FIG. 1, the sensor 211 of FIGS. 2A and 2B, or the sensor 440 of FIG. 4), a communication circuit (not shown, e.g., the communication module 190 of FIG. 1 or the communication circuit 420 of FIG. 4), and a display 750 (e.g., the display module 160 of FIG. 1 or the display 220 of FIGS. 2A, 2B, and 3). According to various embodiments, when the electronic device 700 is a wearable device, the electronic device 700 may further include at least one attachment member (e.g., the attachment members 250 and 260 of FIGS. 2A and 2B) detachably attached to at least a partial region of the housing.

According to an embodiment, the housing of the electronic device 700 may include at least a portion of a conductive portion 710 (e.g., the conductive portion 410 of FIG. 4). For example, the conductive portion 710 may form a side surface and/or at least a portion of a bezel (e.g., the bezel structure 206 of FIGS. 2A and 2B or the side bezel structure 310 in FIG. 3) of the housing of the electronic device 700.

According to an embodiment, the conductive portion 710 may be electrically connected to the communication circuit and the sensor. According to an embodiment, the conductive portion 710 may operate as a biometric electrode of the sensor and an antenna (e.g., the antenna module 197 of FIG. 1, or the first or second antenna 350 or 355 of FIG. 3) of the communication circuit. For example, the conductive portion 710 may operate as at least one of the biometric electrodes of the sensor when being in contact with the user's body.

According to an embodiment, the display 750 may output a user interface indicating that the biosignal of a user is being measured and/or a resulting of measuring the biosignal of a user. For example, when the electronic device 700 measures a user's biosignal (e.g., ECG) through a sensor, the electronic device 700 may measure the biosignal of the user by using the conductive portion 710 of the housing and a separately provided electrode (e.g., the first or second electrode region 213 or 214 of FIG. 2B).

According to an embodiment, the housing of the electronic device 700 may include a first surface (e.g., the first surface 210A of FIGS. 2A and 2B) through which the display 750 is exposed, a second surface (e.g., the second surface 210B of FIGS. 2A and 2B) facing in an opposite direction to the first surface, and a side surface (e.g., the side surface 210C of FIGS. 2A and 2B). For example, at least a portion of the side surface may include the conductive portion 710. For example, the electronic device 700 may include at least one electrode exposed through at least a portion of the second surface of the housing. For example, when two electrodes are included in the second surface of the housing, the sensor of the electronic device 700 may use the conductive region and the two electrodes included in the second surface to measure the user's biosignal (e.g., electrocardiogram (ECG)). For example, when measuring a biosignal (e.g., ECG), a more accurate biosignal may be obtained as the area of the biometric electrode is wider. The electronic device 700 according to an embodiment may utilize a side surface (e.g., a bezel) of a housing that occupies a large area in the electronic device 700 as a biometric electrode, so that it is possible to better measure a biosignal.

According to an embodiment, the electronic device 700 may include a processor (not shown, e.g., the processor 120 of FIG. 1). According to an embodiment, the processor may control the display 750 to output the measurement result of the biosignal measured by using the sensor. According to an embodiment, when the processor detects that the user's body is in contact with the conductive portion 710 through a sensor, the processor may reduce radiated power of the communication circuit. For example, when the user's body contacts the conductive portion 710 (e.g., when the user holds the conductive portion 710 with a finger), the voltage applied to the conductive portion 710 may increase. For example, the electronic device 700 may determine whether the user's body is in contact with the conductive portion 710 based on whether the voltage applied to the conductive portion 710 is greater than or equal to a reference voltage value. For example, the processor may reduce the amount of electromagnetic waves applied to the user by reducing the radiated power of the communication circuit while measuring the user's biosignal through the sensor.

The electronic device 700 according to an embodiment may connect the conductive portion 710 to the sensor and the communication circuit such that the conductive region operates as the biometric electrode of the sensor and the antenna of the communication circuit.

Figure 8:
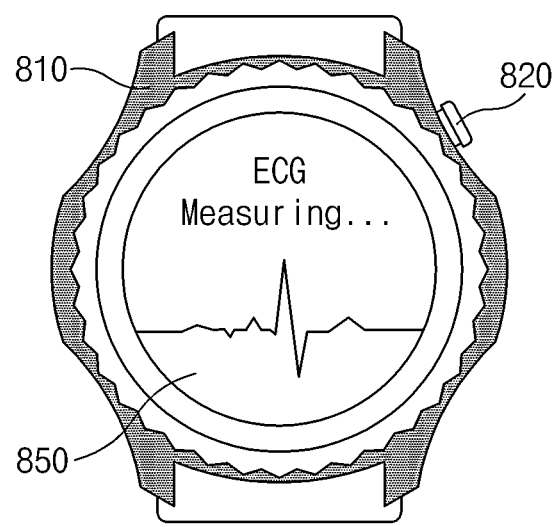
FIG. 8 illustrates an electronic device according to an embodiment of the disclosure.

FIG. 8 illustrates an electronic device according to an embodiment of the disclosure.

Referring to FIG. 8, according to an embodiment, an electronic device 800 (e.g., the electronic device 101 of FIG. 1, the electronic device 200 of FIGS. 2A and 2B, the electronic device 300 of FIG. 3, or the electronic device 400 of FIG. 4) may include a housing (e.g., the housing 210 of FIGS. 2A and 2B), a manipulation unit 820, a sensor (not shown, e.g., the sensor module 176 of FIG. 1, the sensor 211 of FIGS. 2A and 2B, or the sensor 440 of FIG. 4), a communication circuit (not shown, e.g., the communication module 190 of FIG. 1 or the communication circuit 420 of FIG. 4), and a display 850 (e.g., the display module 160 of FIG. 1 or the display 220 of FIGS. 2A, 2B, and 3). For example, the housing of the electronic device 800 may include at least a portion of a conductive portion 810 (e.g., the conductive portion 410 of FIG. 4). For example, the conductive portion 810 may form at least a portion of a side surface and/or a bezel of the housing of the electronic device 800 (e.g., the bezel structure 206 of FIGS. 2A and 2B or the side bezel structure 310 in FIG. 3). According to an embodiment, the conductive portion 810 may be electrically connected to the communication circuit and the sensor.

According to an embodiment, the manipulation unit 820 (e.g., the key input devices 202, 203 and 204 of FIGS. 2A and 2B) may include a key input device (e.g., the key input devices 202, 203 and 204 of FIGS. 2A and 2B). According to an embodiment, the manipulation unit 820 may include a conductor exposed to the outside of the electronic device 800. For example, at least one portion of the manipulation unit 820 may have conductivity. According to an embodiment, the manipulation unit 820 (e.g., a conductor) may be electrically insulated from the conductive portion 810 of the housing. According to an embodiment, the conductive portion 810 and the manipulation unit 820 (e.g., a conductor) may operate as biometric electrodes of the sensor. For example, a plurality of electrodes may be required to measure a biosignal (e.g., ECG or BIA). According to an embodiment, the sensor may measure the user's biosignal by using the conductive portion 810 of the housing and the manipulation unit 820 as biometric electrodes.

According to an embodiment, the electronic device 800 may include a first surface (e.g., the first surface 210A of FIGS. 2A and 2B) through which the display 850 is exposed, a second surface (e.g., the second surface 210B of FIGS. 2A and 2B) facing in an opposite direction to the first surface, and a side surface (e.g., the side surface 210C of FIGS. 2A and 2B). For example, at least a portion of the side surface may include the conductive portion 810. For example, the electronic device 800 includes at least one electrode (e.g., the first electrode region 213 or the second electrode region 214 of FIG. 2B) exposed on at least a portion of the second surface of the housing. For example, when two electrodes are included in the second surface of the housing, the sensor of the electronic device 800 may use the conductive portion 810, the two electrodes included in the second surface and the manipulation unit 820 to measure the user's biosignal (e.g., bioelectrical resistance analysis (BIA)). For example, when the electronic device 800 includes one electrode on the second surface of the housing, the sensor of the electronic device 800 may use the conductive portion 810, the manipulation unit 820, and the electrode on the second surface to measure the user's biosignal (e.g., electrocardiogram (ECG)).

The electronic device 800 according to an embodiment may connect the conductive region to the sensor and the communication circuit such that the conductive region operates as the biometric electrode of the sensor and the antenna (e.g., the antenna module 197 of FIG. 1, or the first antenna 350 or the second antenna 355 of FIG. 3) of the communication circuit.

Figure 9:
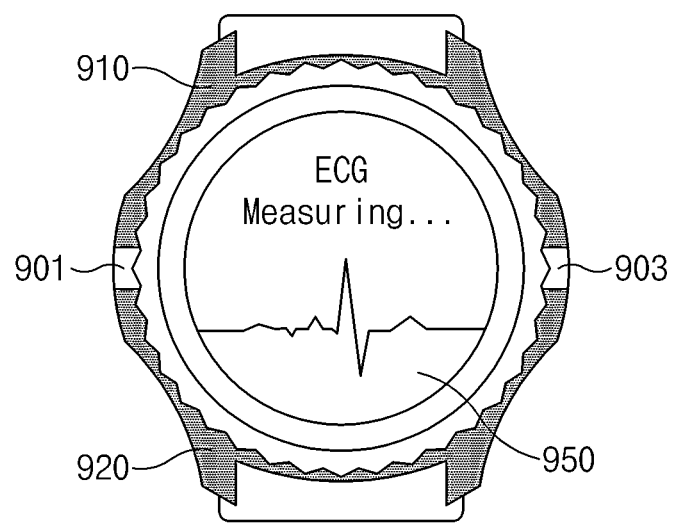
FIG. 9 illustrates an electronic device according to an embodiment of the disclosure.

FIG. 9 illustrates an electronic device according to an embodiment of the disclosure.

Referring to FIG. 9, according to an embodiment, an electronic device 900 (e.g., the electronic device 101 of FIG. 1, the electronic device 200 of FIGS. 2A and 2B, the electronic device 300 of FIG. 3, or the electronic device 400 of FIG. 4) may include a housing (e.g., the housing 210 of FIGS. 2A and 2B), a sensor (not shown, e.g., the sensor module 176 of FIG. 1, the sensor 211 of FIGS. 2A and 2B, or the sensor 440 of FIG. 4), a communication circuit (not shown, e.g., the communication module 190 of FIG. 1 or the communication circuit 420 of FIG. 4), and a display 950 (e.g., the display module 160 of FIG. 1 or the display 220 of FIGS. 2A, 2B, and 3). According to an embodiment, the housing of the electronic device 900 may include at least some of conductive portions 910 and 920 (e.g., the conductive portion 410 of FIG. 4). According to an embodiment, the conductive portion may include the first conductive portion 910 and the second conductive portion 920 spaced apart from each other by electrically insulating portions 901 and 903. For example, the portions 901 and 903 electrically insulating the first conductive portion 910 and the second conductive portion 920 may be arranged between the first conductive portion 910 and the second conductive portion 920. For example, the first conductive portion 910 and the second conductive portion 920 may form at least a portion of a side surface and/or a bezel of the housing of the electronic device 900 (e.g., the bezel structure 206 of FIGS. 2A and 2B or the side bezel structure 310 in FIG. 3). According to an embodiment, each of the first conductive portion 910 and the second conductive portion 920 may be electrically connected to a communication circuit and a sensor. According to an embodiment, at least one of the first conductive portion 910 and the second conductive portion 920 may operate as an antenna of a communication circuit and a biometric electrode of a sensor.

According to an embodiment, the electronic device 900 may include a first surface (e.g., the first surface 210A of FIGS. 2A and 2B) through which the display is exposed, a second surface (e.g., the second surface 210B of FIGS. 2A and 2B) facing in an opposite direction to the first surface, and a side surface (e.g., the side surface 210C of FIGS. 2A and 2B). For example, at least a portion of the side surface may include the first conductive portion 910 and the second conductive portion 920. For example, the electronic device 900 includes at least one electrode (e.g., the first electrode region 213 or the second electrode region 214 of FIG. 2B) exposed on at least a portion of the second surface of the housing. When the electronic device 900 includes two electrodes on the second surface of the housing, the sensor of the electronic device 900 may use one of the first conductive portion 910 and the second conductive portion 920, and two electrodes included in the second surface to measure the user's biosignal (e.g., electrocardiogram (ECG) signal). For example, when the electronic device 900 includes one electrode on the second surface of the housing, the sensor of the electronic device 900 may use the first conductive portion 910, the second conductive portion 920, and the electrode on the second surface to measure the user's biosignal (e.g., electrocardiogram (ECG)).

The electronic device 900 according to an embodiment may connect the first conductive portion 910 and the second conductive portion 920 together to the sensor and the communication circuit such that at least one of the first conductive portion 910 and the second conductive portion 920 operates as the biometric electrode of the sensor and the antenna (e.g., the antenna module 197 of FIG. 1, or the first antenna 350 or the second antenna 355 of FIG. 3) of the communication circuit.

According to an embodiment, the electronic device 900 may display guide information for a user input (e.g., user's body contact with the first conductive portion 910 and/or the second conductive portion 920) received through the first conductive portion 910 and/or the second conductive portion 920 on the display 950. For example, when measuring biometric information, the electronic device 900 may display a user interface (UI) for prompting the user to contact the user's body in a region adjacent to the first conductive portion 910 and/or the second conductive portion 920. The user interface may be maintained while the biometric information is measured, and the user interface may also be terminated when the measurement is finished.

Figure 10:
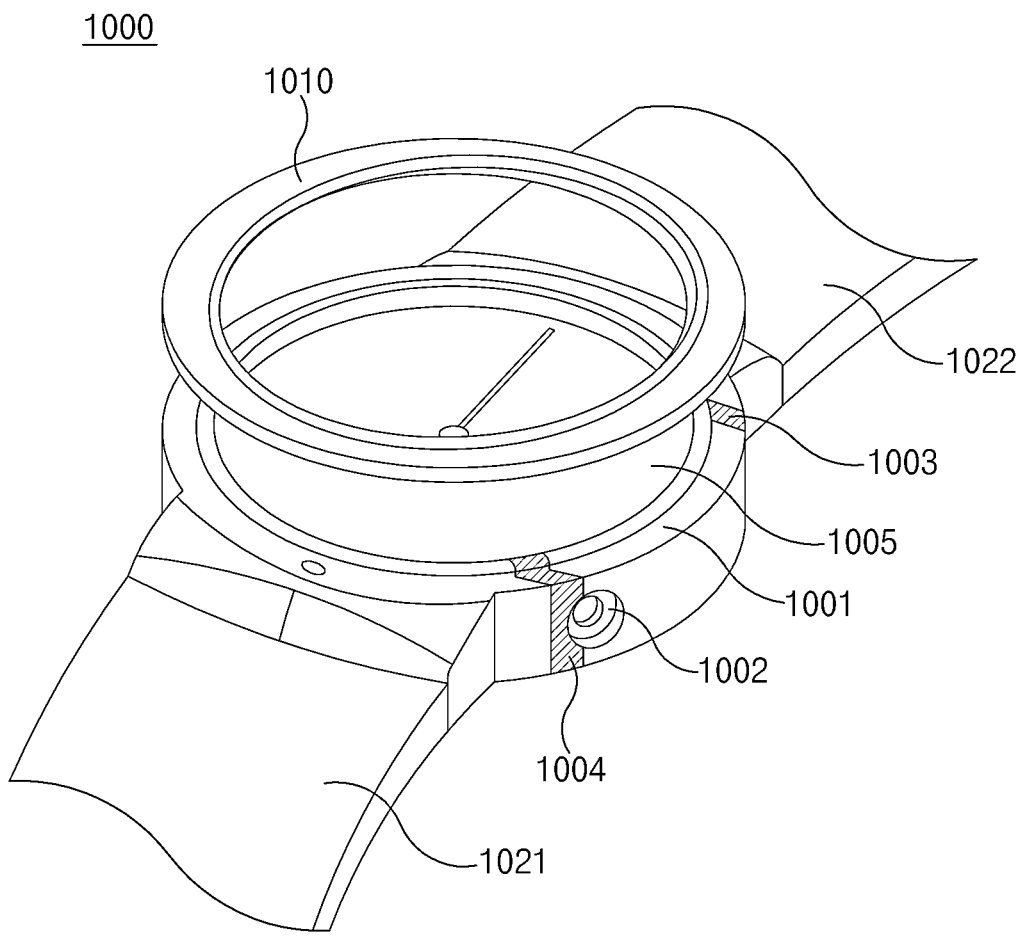
FIG. 10 illustrates an electronic device according to an embodiment of the disclosure.

FIG. 10 illustrates an electronic device according to an embodiment of the disclosure.

Referring to FIG. 10, according to an embodiment, an electronic device 1000 (e.g., the electronic device 101 of FIG. 1, the electronic device 200 of FIGS. 2A and 2B, the electronic device 300 of FIG. 3, or the electronic device 400 of FIG. 4) may include a housing 1001 (e.g., the housing 210 of FIGS. 2A and 2B), a sensor (not shown, e.g., the sensor module 176 of FIG. 1, the sensor 211 of FIGS. 2A and 2B, or the sensor 440 of FIG. 4), a communication circuit (not shown, e.g., the communication module 190 of FIG. 1 or the communication circuit 420 of FIG. 4), a display 1005, a bezel wheel 1010, and coupling members 1021 and 1022. According to an embodiment, a hole 1002 in which segmental portions 1003 and 1004 and the crown are mounted may be formed in the housing 1001. According to an embodiment, the housing 1001 may include a conductive portion (e.g., the conductive portion 410 of FIG. 4). For example, the housing 1001 may be a metal, such as stainless steel (SUS). According to an embodiment, the coupling members 1021 and 1022 configured to be detachable to a portion of the user's body may be connected to one side of the housing 1001. For example, the material of the coupling members 1021 and 1022 may be leather, urethane or ceramic. According to an embodiment, the housing 1001 may include a side surface surrounding at least a portion of the display 1005.

According to an embodiment, the segmental portions 1003 and 1004 may be formed of a non-metallic material. According to an embodiment, the housing 1001 may have capacitance formed by the segmental portions 1003 and 1004, and may be divided into a first conductive portion and a second conductive portion with the segmental portions 1003 and 1004 interposed therebetween. According to an embodiment, each of the first conductive portion and the second conductive portion may operate as a first antenna and a second antenna. According to an embodiment, the resonant frequencies of the first antenna and the second antenna may be changed by at least one of the distance between the segmental portions 1003 and 1004, the segment position, the permittivity combination according to the materials of the segmental portions, and the thickness of the segmental portion itself. According to an embodiment, at least one of the first conductive portion and the second conductive portion may be used as an electrode for measuring a biosignal. According to an embodiment, a graphic object (e.g., a clock minute hand, and the like) may be displayed on the display 1005.

According to an embodiment, at least one conductive portion (e.g., a first conductive portion and/or a second conductive portion) included in the housing of the electronic device 1000 may commonly operate as an antenna and an electrode for measuring a biosignal.

Figure 11A:
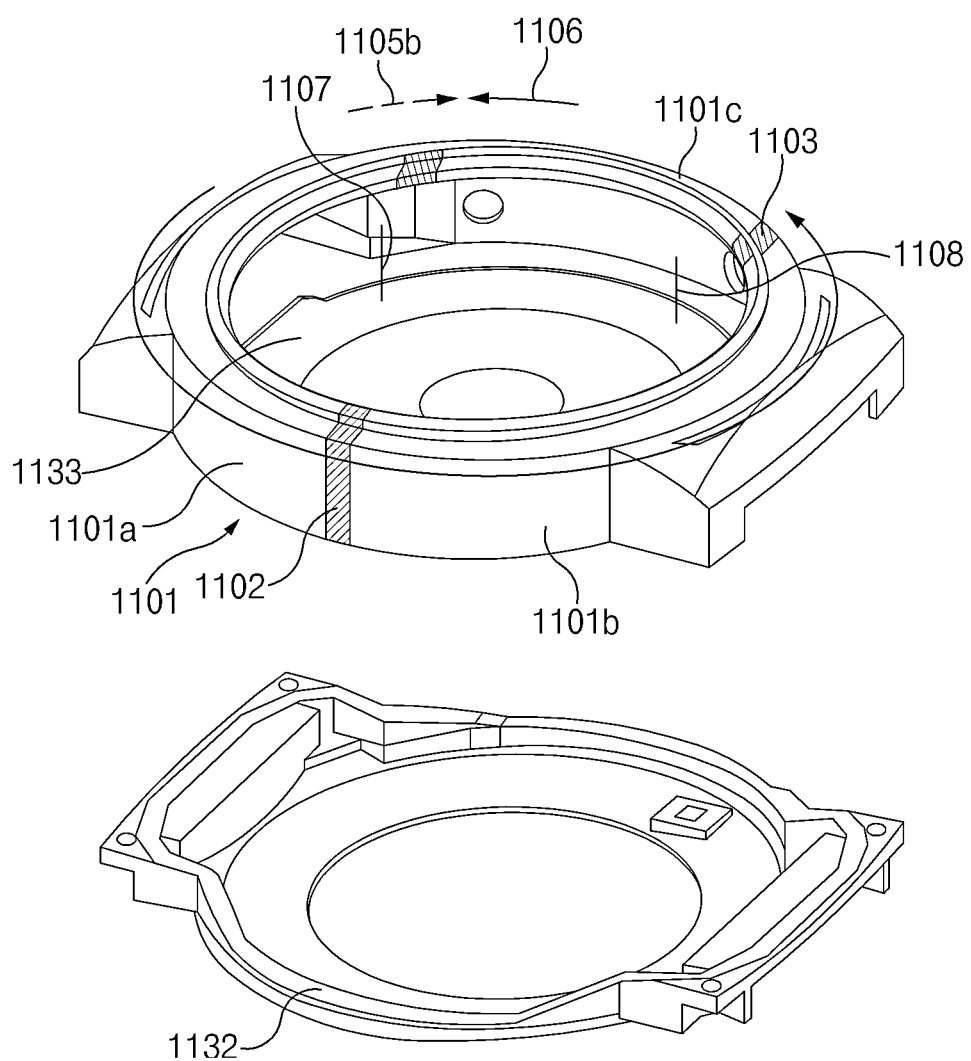
FIGS. 11A and 11B illustrate an electronic device according to various embodiments of the disclosure.
Figure 11B:
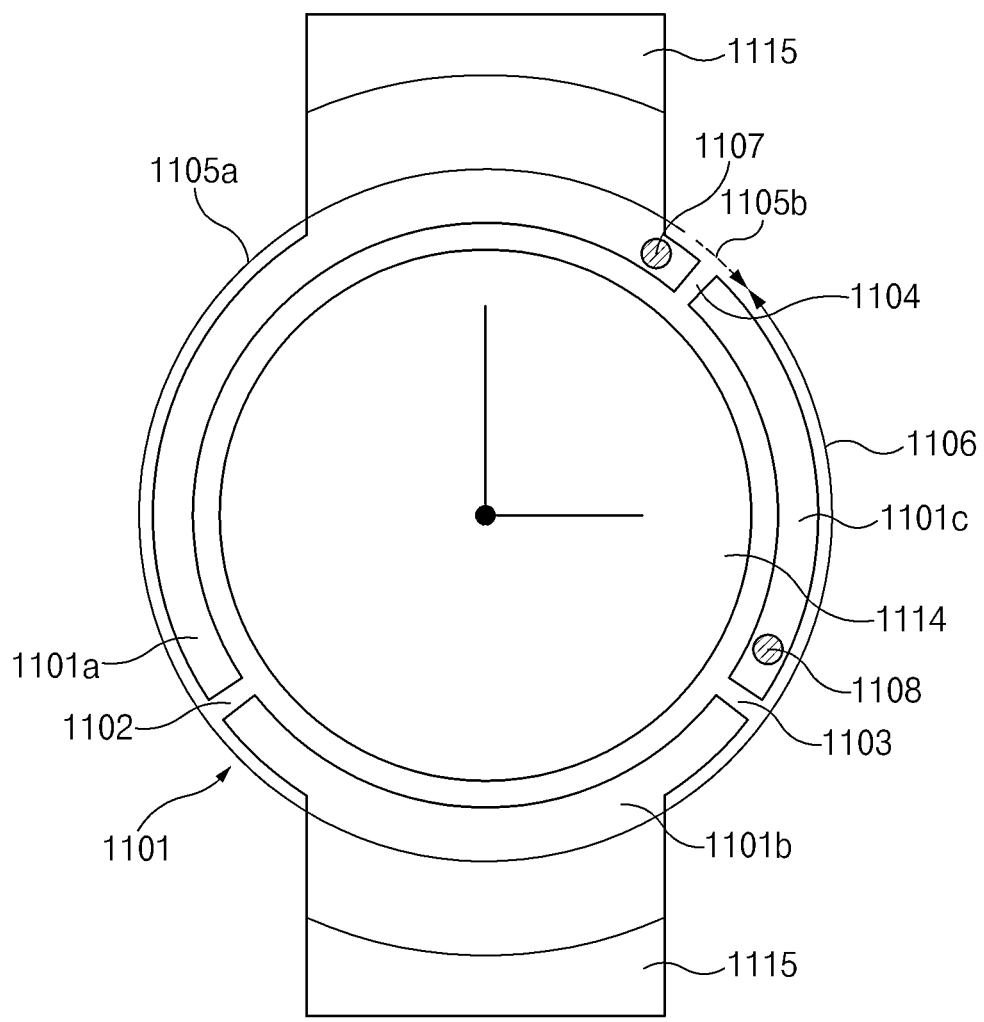

FIGS. 11A and 11B illustrate an electronic device according to various embodiments of the disclosure.

According to an embodiment, an electronic device 1100 (e.g., the electronic device 101 of FIG. 1, the electronic device 200 of FIGS. 2A and 2B, the electronic device 300 of FIG. 3, or the electronic device 400 of FIG. 4) may include a housing 1101 (e.g., the housing 210 of FIGS. 2A and 2B), a sensor (not shown, e.g., the sensor module 176 of FIG. 1, the sensor 211 of FIGS. 2A and 2B, or the sensor 440 of FIG. 4), a communication circuit (not shown, e.g., the communication module 190 of FIG. 1 or the communication circuit 420 of FIG. 4), a substrate 1133, and a rear cover 1132. According to an embodiment, the housing 1101 may include a first conductive portion 1101*a*, a second conductive portion 1101*b*, or a third conductive portion 1101*c* divided by a plurality of segmental portions 1102, 1103 and 1104. According to an embodiment, the segmental portion 1102 may be a first non-conductive portion. The segmental portion 1103 may be a second non-conductive portion. The segmental portion 1104 may be a third non-conductive portion 1104.

According to various embodiments, the first conductive portion 1101*a* may be electrically connected to a communication module of the substrate 1133 by a first feeding portion 1107. The third conductive portion 1101*c* may be electrically connected to the communication module of the substrate 1133 by a second feeding portion 1108. According to an embodiment, at least one of the first conductive portion 1101*a*, the second conductive portion 1101*b*, and the third conductive portion 1103*c* may operate as an antenna (or radiator). According to an embodiment, the resonant frequency of the antenna may be changed according to the size, position, material, and number of the segmental portions 1102, 1103 and 1104. According to an embodiment, the resonant frequency of the antenna may be changed according to the positions of the first and second feeding portions 1107 and 1108.

According to various embodiments, the housing 1101 may operate as a multi-band antenna operating in various bands. According to an embodiment, the first and second conductive portions 1101*a* and 1101*b*, the segmental portion 1102, and the feeding portion 1107 may be used as a radiator operating in a first frequency band of the first antenna. According to an embodiment, the radiator may have a radiation current 1105*a* that is fed from the first feeding portion 1107 and radiated through the first conductive portion 1101*a*, the segmental portion 1102, and the second conductive portion 1101*b*. According to an embodiment, the first radiator may resonate in a low frequency band and a multiplication high frequency band. According to an embodiment, the first and third conductive portions 1101*a* and 1101*c*, the segmental portion 1104, and the feeding portion 1107 may be used as a radiator operating in the second frequency band of the first antenna. According to an embodiment, the radiator may have a radiation current 1105*b* that is fed from the first feeding portion 1107 and radiated through the first conductive portion 1101*a*, the segmental portion 1104, or the third conductive portion 1101*c*. According to an embodiment, the radiator may resonate in a high frequency band. According to an embodiment, the third conductive portion 1101*c* and the second feeding portion 1108 may be utilized as a radiator of the second antenna. The radiator may have a radiation current 1106 that is fed from the second feeding portion 1108 and radiated through the third conductive portion 1101*c*.

According to various embodiments, the first radiation current 1105*a* and the second radiation current 1105*b* of the first antenna may operate as an antenna for receiving a mobile communication band, and the radiation current 1106 of the second antenna may operate as an antenna for receiving a Bluetooth band.

According to various embodiments, the resonant frequency of the antenna may be changed according to the size, position, material (e.g., permittivity), and number of the segmental portions 1102, 1103 and 1104. According to an embodiment, the substrate 1133 may be electrically connected to the housing 1101. A feeding portion (not shown) corresponding to the feeding portions 1107 and 1108 of the housing may be formed on the substrate 1133. The feeding portion formed on the substrate 1133 may include a metal member (e.g., a C-clip, a metal spring, or the like) having elasticity. According to an embodiment, a separate electrical connection member may be interposed between the housing 1101 and the substrate 1133. According to an embodiment, the electrical connection member may include one or more of various members, such as a session cable (e.g., metal wire), a flexible printed circuit, a C-clip, a conductive gasket, or the like.

According to an embodiment, at least one of the first conductive portion 1101*a*, the second conductive portion 1101*b*, and the third conductive portion 1101*c* may be used as an electrode for measuring a biosignal. For example, when at least one of the first conductive portion 1101*a*, the second conductive portion 1101*b*, and the third conductive portion 1101*c* is in contact with the user's body, the sensor circuit may operate as an electrode for measuring a biosignal of a user.

According to various embodiments, a coupling member 1115 configured to be detachable to a portion of the user's body may be connected to one side of the housing 1101. According to an embodiment, the housing 1101 may be arranged such that at least a portion of the housing 1101 is exposed to an outside of the electronic device 1100.

According to an embodiment, at least one conductive portion (e.g., the first conductive portion 1101*a*, the second conductive portion 1101*b*, and/or the third conductive portion 1101*c*) included in the housing of the electronic device 1100 may be commonly operated as an antenna and an electrode for measuring a biosignal.

According to an embodiment of the disclosure, an electronic device may include a housing including at least a portion of a conductive portion, a display 1114 visually exposed to an outside through at least a portion of the housing, a communication circuit electrically connected to the conductive portion, a sensor electrically connected to the conductive portion, a first blocking circuit connected between the conductive portion and the communication circuit and configured to block a signal in a first frequency range, a second blocking circuit connected between the conductive portion and the sensor to block a signal in a second frequency range, and a processor operatively connected to the display, the communication circuit and the sensor, wherein the conductive portion is configured to operate as an antenna of the communication circuit and a biometric electrode of the sensor.

According to an embodiment, the first blocking circuit may include at least one capacitor, and the second blocking circuit may include at least one inductor.

According to an embodiment, the first frequency range may be a higher frequency range than the second frequency range.

According to an embodiment, the conductive portion may be configured to form at least a portion of a side surface of the electronic device.

According to an embodiment, the conductive portion may constitute a bezel of the electronic device According to an embodiment, the electronic device may further include at least one electrode spaced apart from the conductive portion. According to an embodiment, the processor may measure a biosignal of a user contacting the conductive portion and the at least one electrode through the sensor.

According to an embodiment, the at least one electrode may be arranged to be exposed to an outside through one surface of the housing facing in an opposite direction to the display.

According to an embodiment, the conductive portion may include a first conductive portion and a second conductive portion that are arranged to be spaced apart from each other.

According to an embodiment, the electronic device may further include a manipulation unit arranged on at least a portion of a side surface of the housing and including a conductor exposed to an outside. According to an embodiment, the conductor may be configured to operate as the biometric electrode of the sensor.

According to an embodiment, the conductor may be electrically insulated from the conductive portion.

According to an embodiment, the biosignal may include an electrocardiogram (ECG), a galvanic skin response (GSR), an electroencephalogram (EEG) or a bioelectrical impedance analysis (BIA) signal.

According to an embodiment, the processor may be configured to reduce radiation power of the communication circuit when detecting contact of a body of the user with the conductive portion through the sensor.

According to an embodiment of the disclosure, an electronic device may include a housing including a first surface, a second surface facing in an opposite direction to the first surface, and a side surface including at least a portion of a conductive portion, at least one attachment member detachably attached to at least an area of the housing, a display visually exposed to an outside through at least a portion of the first surface, a sensor including at least one biometric electrode exposed to an outside through at least a portion of the second surface, a communication circuit electrically connected to the conductive portion, a sensor electrically connected to the conductive portion, a first blocking circuit connected between the conductive portion and the communication circuit to block a signal in a first frequency range, a second blocking circuit connected between the conductive portion and the sensor to block a signal in a second frequency range, and a processor operatively connected to the display, the communication circuit and the sensor, wherein the conductive portion may be configured to operate as an antenna of the communication circuit and a biometric electrode of the sensor.

According to an embodiment, the second frequency range may be a higher frequency range than the first frequency range.

According to an embodiment, the first blocking circuit may include at least one capacitor, and the second blocking circuit may include at least one inductor.

According to an embodiment, the side surface may include a first side surface including a first conductive portion and a second side surface including a second conductive portion, and the first conductive portion is electrically insulated from the second conductive portion.

According to an embodiment, an electronic device may further include an input device arranged on at least a portion of the side surface and including at least a portion of an additional conductive portion, and the additional conductive portion may be configured to operate as an additional biometric electrode of the sensor.

According to an embodiment, the conductive portion may be electrically insulated from the additional conductive portion.

According to an embodiment, the biosignal may include an electrocardiogram (ECG), a galvanic skin response (GSR), an electroencephalogram (EEG) or a bioelectrical impedance analysis (BIA) signal.

According to an embodiment, the processor may be configured to control the display to output a biosignal measurement result measured by using the sensor.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used in connection with various embodiments of the disclosure, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., an internal memory 136 or an external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., a compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. An electronic device comprising:
    a housing including conductive portions, wherein the conductive portions include a first conductive portion and a second conductive portion forming at least a portion of a side surface of the housing;
    a display visually exposed to an outside through at least a portion of the housing;
    a communication circuit electrically connected to the conductive portions;
    a sensor electrically connected to the conductive portions;
    a first blocking circuit connected between the conductive portions and the communication circuit and configured to block a signal in a first frequency range;
    a second blocking circuit connected between the conductive portions and the sensor to block a signal in a second frequency range; and
    a processor operatively connected to the display, the communication circuit, and the sensor,
    wherein the first conductive portion and the second conductive portion are configured to operate as an antenna of the communication circuit and a biometric electrode of the sensor, and
    wherein the side surface includes electrically insulating portions arranged between the first conductive portion and the second conductive portion and electrically insulating the first conductive portion from the second conductive portion.

2. The electronic device of claim 1,
    wherein the first blocking circuit includes at least one capacitor, and
    wherein the second blocking circuit includes at least one inductor.

3. The electronic device of claim 1, wherein the first frequency range is a higher frequency range than the second frequency range.

4. The electronic device of claim 1, wherein the conductive portions constitute a bezel of the electronic device.

5. The electronic device of claim 1, further comprising:
    at least one electrode spaced apart from the first conductive portion and the second conductive portion,
    wherein the processor is configured to measure a biosignal of a user contacting the at least one electrode through the sensor and at least one of the first conductive portion or the second conductive portion.

6. The electronic device of claim 5, wherein the at least one electrode is arranged to be exposed to an outside through one surface of the housing facing in an opposite direction to the display.

7. The electronic device of claim 1, wherein the first conductive portion and the second conductive portion that are arranged to be spaced apart from each other.

8. The electronic device of claim 1, further comprising:
    a manipulation unit arranged on at least a segment of the side surface of the housing and including a conductor exposed to an outside,
    wherein the conductor is configured to operate as the biometric electrode of the sensor.

9. The electronic device of claim 8, wherein the conductor is electrically insulated from the first conductive portion and the second conductive portion.

10. The electronic device of claim 5, wherein the biosignal includes an electrocardiogram (ECG), a galvanic skin response (GSR), an electroencephalogram (EEG) or a bioelectrical impedance analysis (BIA) signal.

11. The electronic device of claim 5, wherein the processor is configured to reduce radiation power of the communication circuit when detecting contact of a body of the user with at least one of the first conductive portion or the second conductive portion through the sensor.

12. An electronic device comprising:
a housing including a first surface, a second surface facing in an opposite direction to the first surface, and a side surface including conductive portions, wherein the conductive portions include a first conductive portion and a second conductive portion forming at least a portion of the side surface;
at least one attachment member detachably attached to at least an area of the housing;
a display visually exposed to an outside through at least a portion of the first surface;
a sensor, electrically connected to the conductive portions, including at least one biometric electrode exposed to the outside through at least a portion of the second surface;
a communication circuit electrically connected to the conductive portions;
a first blocking circuit connected between the conductive portions and the communication circuit to block a signal in a first frequency range;
a second blocking circuit connected between the conductive portions and the sensor to block a signal in a second frequency range; and
a processor operatively connected to the display, the communication circuit, and the sensor,
wherein the first conductive portion and the second conductive portion are configured to operate as an antenna of the communication circuit and a biometric electrode of the sensor, and
wherein the side surface includes electrically insulating portions arranged between the first conductive portion and the second conductive portion and electrically insulating the first conductive portion from the second conductive portion.

13. The electronic device of claim 12, wherein the second frequency range is a higher frequency range than the first frequency range.

14. The electronic device of claim 12,
wherein the first blocking circuit includes at least one capacitor, and
wherein the second blocking circuit includes at least one inductor.

15. The electronic device of claim 12, further comprising:
an input device arranged on at least a segment of the side surface and including at least a portion of an additional conductive portion,
wherein the additional conductive portion is configured to operate as an additional biometric electrode of the sensor.

16. The electronic device of claim 15, wherein the first conductive portion and the second conductive portion are electrically insulated from the additional conductive portion.

17. The electronic device of claim 12,
wherein the sensor measures a biosignal of a user contacting the at least one biometric electrode and at least one of the first conductive portion or the second conductive portion, and
wherein the biosignal includes an electrocardiogram (ECG), a galvanic skin response (GSR), an electroencephalogram (EEG) or a bioelectrical impedance analysis (BIA) signal.

18. The electronic device of claim 17, wherein the processor is configured to control the display to output a biosignal measurement result measured by using the sensor.

19. The electronic device of claim 1,
wherein the first conductive portion forms part of the side surface surrounding an upper half of the housing,
wherein the second conductive portion forms part of the side surface surrounding a lower half of the housing, and
wherein the upper half of the housing and the lower half of the housing are separated by the electrically insulating portions.

* * * * *